United States Patent [19]

Kinoshita et al.

[11] 4,370,558
[45] Jan. 25, 1983

[54] FILM BLACKENING AREA MEASURING EQUIPMENT

[75] Inventors: Minoru Kinoshita, Kyoto; Masaji Mizuta, Uji, both of Japan

[73] Assignee: Dainippon Screen Mfg. Co., Ltd., Kyoto, Japan

[21] Appl. No.: 253,675

[22] Filed: Apr. 13, 1981

[30] Foreign Application Priority Data

Apr. 30, 1980 [JP] Japan ............................... 55-058531

[51] Int. Cl.³ ............................................ G01N 21/59
[52] U.S. Cl. ..................................... 250/559; 356/443
[58] Field of Search ................. 250/559; 356/443, 444

[56] References Cited

U.S. PATENT DOCUMENTS 4,293,226 10/1981 Kinoshita et al. ................... 356/443

Primary Examiner—David C. Nelms
Assistant Examiner—Darwin R. Hostetter
Attorney, Agent, or Firm—Brumbaugh, Graves, Donohue & Raymond

[57] ABSTRACT

An amplification-factor of the amplifier is controlled so as the output from a film-detecting-mechanism to be supplied as the input into a subtractor is adjusted fitting to a reference signal-prior to the film-insertion into the detecting mechanism. The output-signal from a comparator is supplied into the amplification-factor-variable-amplifier, in which the amplification-factor is controlled depending on the magnitude of the input-signal, and it is kept at the controlled value.

Or an intensity of a light source is controlled so as the output from the film detecting mechanism to be supplied as the input into the subtractor is adjusted fitting to the reference-signal prior to the film-insertion into the detecting mechanism.

2 Claims, 10 Drawing Figures

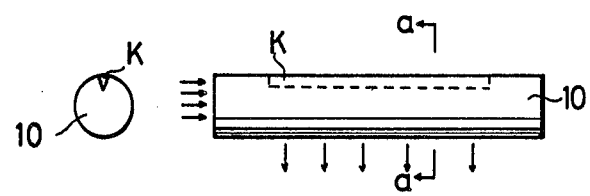
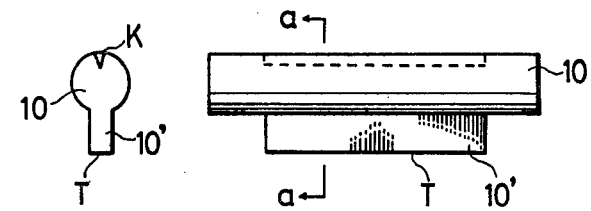
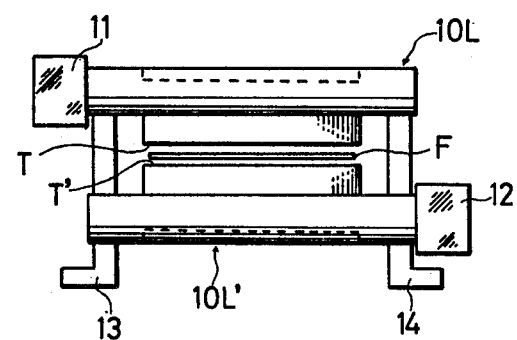

FILM BLACKENING AREA MEASURING EQUIPMENT

BACKGROUND OF THE INVENTION

The present invention relates to a film blackening area measuring equipment which is applicable, for instance, as a part of the liquid replenishing device for a film processor.

To film processor of conventional type, a device to keep the processing ability at a constant level with replenisher i.e. liquid replenishing device is provided to prevent the processing ability from being lowered since the developer is deteriorated as the developing work proceeds. This relenisher is so designed to judge the degree of liquid deterioration by measuring the extent of film blackening area and to replenish the liquid based on the result of film blackening area measurement.

An example of film processor is outlined in FIG. 1. Referring to FIG. 1, in a developing tank 1 developing solution A is filled, fixing solution B is supplied in a fixation tank 2, and water C is contained in a washing tank 3. Further a drying tank 4 is provided following to the washing tank 3. The detectors 7, 8 are respectively provided to detect insertion of film F and the advance into the blackening area measuring equipment, more specifically, these are micro switches and others. An exposed film F is inserted through the inlet 5 and is transferred to the respective tanks 1, 2, 3, 4 in order along the route f (indicated by the alternate long and short dash line) while being intermediated by the guide mechanism as illustrated in the drawing. After being treated for development, the film is discharged to the film-receiving-tray 9 out of the drying tank 4. The blackening-area-measuring-equipment M related to the present invention for the film F is ordinarily placed between the washing tank 3 and the drying tank 4. The ouput signal from this blackening-area-measuring-equipment M is input to the liquid replenisher 6, by which the required chemical liquids are replenished to the respective tanks so as to prevent the processing ability from being lowered.

While the film-blackening-area-measuring-equipment M is composed of a projector having the even light distribution to the whole part of the maximum effective width (the dimension in the direction perpendicular to the film advancing direction) of the film F, and of a receiver so arranged to face the projector with the film advancing route in-between. For measurement of the blackening area of the film F, the light quantity coming into the receiver corresponding to the degree of the blackening area of the film F is measured, and the difference in the received light quantity between the time of no film passing through and the time when the film F of certain degree of the blackening area is inserted between the projector and the receiver is calculated.

As the projector, any device may be applicable only if it has the function to apply light evenly on the film F along the maximum width of the film to be treated. As the receiver, any device may also be used only if it functions to detect the light quantity applied by the projector through the film F.

Proposed here is quite a favourable equipment as the projector and receiver for this type of device. Shown in FIG. 2 to FIG. 4 are the example of principle and structure of such projector and receiver. A round bar 10 (circular cylinder) is made of glass or plastic, and when the light is applied from one end of it, the major portion of the light goes out of the other end of it after repeating total reflection though the minor portion of the light goes out of the peripheral surface of the circular cylinder. A V-shape groove k, having a coase surface, provided on the peripheral surface of this cylinder in parallel with the shaft center as shown in FIG. 2-a which shows a—a section, makes a part of the light radiated from the left end reflected on the groove surface and diffused by irregular reflection to generate the light at the right angles to the shaft center. And the light diffused by irregular reflection goes out through the surface of the opposite side of the groove k. If a plate 10'0 is made solid to or attached to the round bar 10 at the outlet side of the light as shown in FIG. 3-a and FIG. 3-b, the radiation efficiency through the surface T is improved compared with the case of FIG. 2, and the orientation is also intensified. To improve the reflection on the surface of the V-groove k, plating of the surface or coating of white pigment may be employed effectively. The plate 10' might be called a light conductor, and when the light is applied inversely from the end surface T of the plate unit 10', the light reflected irregularly on the groove surface of the round bar 10 comes out from the end of it. If a photo-electric converter element is provided at the end of the light conducting bar 10, therefore, quantity of the incident light from the end surface of the plate unit can be measured. Not all the light quantity from the plate unite 10' goes out of the round bar end, but a proportional relation is established between the incident light quantity and radiated light quantity.

By providing two light conductors with such characteristics in such a matter that the end surfaces T are faced each other, a film detecting mechanism suitable to detect the light quantity that has passed through a film can be realized. FIG. 4 shows an example of such film detecting mechanism, in which two light conductors 10L, 10L' are placed with their end surfaces T, T' facing each other and with an adequate spacing to allow the film F to go through, which are respectively mounted on flames 13, 14. On an end of the round bar at projector side, a light source 11 is attached, and on an end of the round bar at the opposite side of the receiver round bar, a receiver 12 is installed. With a detecting mechanism composed in this manner, when a film F is inserted between the two end surfaces T, T' and is advanced while radiating the light from the light source 11, the receiver 12 receives the light in the quantity proportional to the transmission rate of the film, and the output of the electrical signal in proportion to the light quantity is given. A film-blackening-area-measuring-equipment is made by composing the equipment so as the output signal from the receiver 12 is taken out as the film-blackening-area-signal. FIG. 5 shows an example of such equipment. The composition is so made that the output from the receiver 12 is supplied as the input to the amplifier 16, and the output from the amplifier 16 is further supplied to the variable resister 19 for adjustment. Then the input from the receiver 12 under the condition before a film F is inserted into the detection mechanism to the subtractor 18 is adjusted to the reference signal from the reference signal generator 17. Accordingly, the output from the subtractor 18 is zero before insertion of the film F. When the film F with certain degree of the blackening area is inserted into the detecting mechanism under this condition, the signal in proportion to the blackening area of the film is to be given as the output from the subtractor 18. The blackening area of the film is measured as the output value. With the measurement by this system, however, the light conductor 10L at the light source side may sometimes be deformed due to variation in the light intensity of the light source 11 or due to other external causes such as heat. As a disadvantage, therefore, the projected light quantity changes at time goes due to the above mentioned deformation and other reasons, and the output from the subtractor differs from the actual blackening area degree. To improve such disadvantages, the mechanism as shown in FIG. 6 is supplied. To the equipment shown in FIG. 6, another light receiver 15 is also provided at the end of the light conductor 10L at the side of the light source. Before starting the film detection, the input from the light source side receiver 15 to the subtractor 18 is adjusted to the equal level as the input from the receiving side receiver 12 to the subtractor 18. For this equipment, the output of the receiver 15 is used as the reference signal of the equipment shown in FIG. 5, and by this arrangement, the problem of accuracy due to deformation or strain of the light conductor is improved. Even with this equipment, however, the same trouble in accuracy as that of FIG. 5 is caused when the extent of deformation differs more or less between the two light conductors. Another defect is that errors are caused on the measurement when the two conductors 10L, 10L' are strained by a wet film passing between the light conductors 10L, 10L'. Besides the above, trial for exact film blackening area measurement with various types of control such as the integration of the output signal from the said film detecting mechanism have been proposed so far. In any one of such trials, however, no consideration is paid to the deformation due to external causes such as temperature of the detecting mechanism, which radiate a specified quantity of the light on a film and generates the output signal proportional to the blackening area extent by receiving the transmitted light through the film as described above. As the present situation, therefore, the problems as described above are not solved basically yet.

BRIEF SUMMARY OF THE INVENTION

The present invention is to offer an accurate blackening-area-measuring-equipment of films which can improve the defects of the conventional equipments and is free from any time-bound variation.

The above and further objects and novel features of the invention will more fully appear from the following detailed description when the same is read in connection with the accompanying drawings. It is to be expressly understood, however, that the drawings are for purpose of illustration only and are not intended as a definition of the limits of the invention.

BRIEF DESCRIPTION OF THE DRAWINGS

FIGS. 2a and 2b and FIGS. 3a and 3b are the schematic plan view of the light conductors as the principal components of a film detecting mechanism, FIG. 4 is the schematic plan view of the film detecting mechanism.

DETAILED DESCRIPTION OF THE INVENTION

Figure 1:
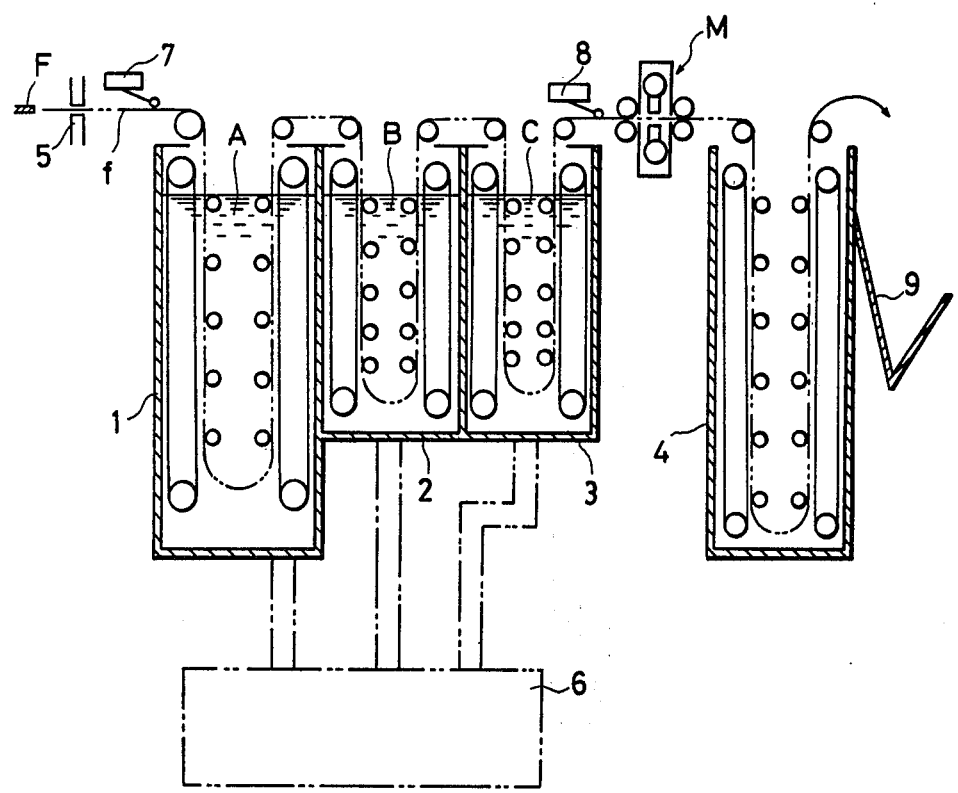
FIG. 1 is a schematic representation to show the structure of a film processor.
Figure 7:
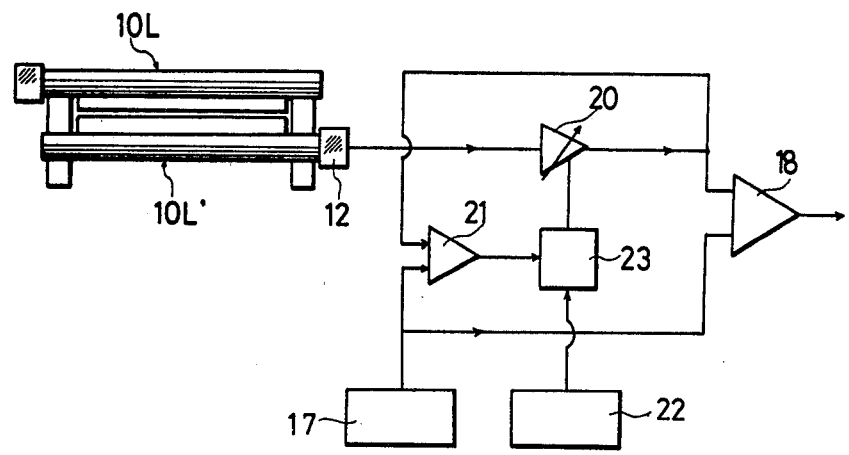
FIG. 7 is the schematic block diagram according to the invention to show an embodiment of the film-blackening-area-measuring-equipment.

Referring to FIG. 7, the film-blackening-area-measuring-equipment according to this invention so composed that the output from the receiver is amplified and adjusted fitting to the reference-signal-output before film insertion into the detecting mechanism. The amplification factor after adjustment is held by insertion of a film and film-blackening-area-measurement is carried out. That is, an amplifier of amplification-factor-variable-type 20 is to be controlled and adjusted in proportion to the control-input of electrical signal received. Accordingly, the output from the receiver 12 is amplified by this amplification-variable-type-amplifier 20, supplied as the input into the subtractor 18, and the difference with the reference signal from the reference-signal-generator 17, which is then taken out as the blackening-area-signal. According to the present invention, the output of the said amplifier 20, before a film is inserted into the film detecting mechanism composed of two light conductors 10L, 10L', is first supplied to the comparator 21 for the comparison with the reference signal, and the output is supplied to the amplifier 20 through the adjusting circuit 23. The amplification factor is adjusted corresponding to the magnitude of the input signal, thus the output of the amplification factor from the amplifier becomes equal to the magnitude of the reference signal. The output of the subtractor 18, therefore, becomes zero at this time. The generator of film-feed-signal 22 is composed of the detectors 7, 8 shown in FIG. 1. When a film F is inserted, the film-feed-signal is supplied to the adjusting circuit 23, and the supply of the output from the comparator 21 into the amplifier 20 is suspended. As the input is suspended, the adjusting operation comes to stop, and the amplification factor of the amplifier 20 is fixed at the ratio when the film signal is generated. After fixation of the amplification factor, the output from the receiver 12 is processed by the accurately adjusted amplifier to perform measurement of the film-blackening-area accurately.

Figure 5:
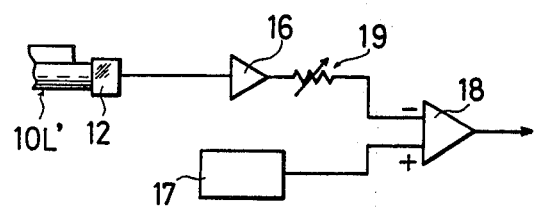
FIG. 5 and FIG. 6 are the schematic circuit diagrams of a conventional type film-blackening-area-measuring-equipment.
Figure 6:
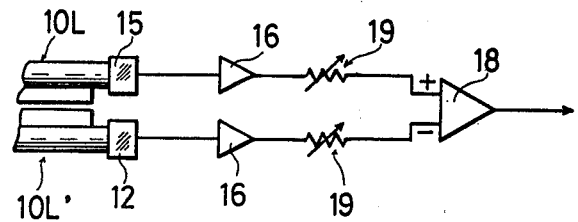
Figure 8:
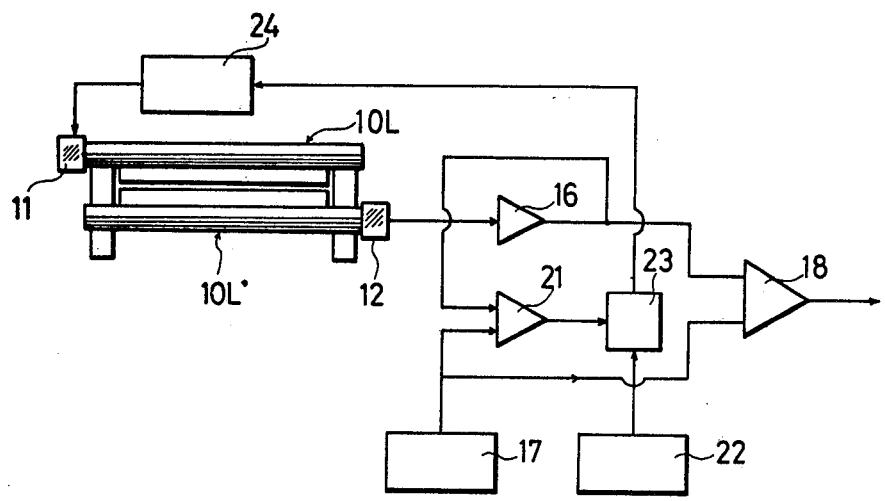
FIG. 8 is the schematic block diagram according to this invention to show the second embodiment of the film-blackening-area-measuring-equipment.

Referring to FIG. 8, which shows the second embodiment according to this invention, the film-blackening-area-measuring-equipment is so composed that the film detecting mechanism i.e. the light-source-intensity of the light conductors is adjusted in order to put the output from the receiver 12 before film insertion in line with the reference-signal-output, the light-source-intensity after adjustment is maintained by film insertion so as to perform the blackening-area-measurement. More particularly, a fixed-type-amplifier 16 is similar to that of FIG. 5 and FIG. 6, and the output is supplied to the comparator 21 to be compared with the reference signal. Any difference detected through the comparison is supplied as the input to the light-source-controller 24 through the adjusting circuit 23. By this light-source-controller 24, the intensity of the light source 11 of the light conductor 10L is adjusted, and the output from the receiver 12 is made equal to the reference signal. A film-feed-signal-generator 22 generates signal-output when a film is inserted beween the two light conductors 10L, 10L', and the supply of the output from the comparator 21 into the light-source-controller 24 is suspended. Then the light-source-intensity at the point of film insertion is maintained for light projection, thus the film-blackening-area-measurement is performed.

The film-blackening-area-measuring-equipment of the first embodiment according to the present invention is as shown in FIG. 7, but is not limited therein. As the adjusting system of the amplification factor by the output from a comparator, for example, such method may also be employed that a motor is turned by the output from the comparator to control the amplification factor of the amplifier by the motor rotation besides the system to control the amplifier itself by the input of the electrical signal like the case as illustrated. The adjusting mechanism to stop and to hold the amplification-factor-variation of the amplification mechanism by insertion of a film is not limited to the illustrated embodiment either. For instance, the adjusting mechanism can be a switching mechanism or a change-over circuit, and it may also possible to compose the adjusting mechanism as a combined solid unit of the adjusting circuit and the film-feed-signal-generator. Mechanical adjusting mechanism may also be possible, and the present invention includes all of these embodiments.

Now the film-blackening-area-measuring-equipment of the second embodiment according to the present invention is so composed as illustrated in FIG. 8, but here again, the invention is not limited to the illustrated embodiment. As the control and adjust mechanism of the light-source-intensity by the output from the comparator, for example, a number of different types of controllers are available. It is also possible to employ a control system of the input energy into the light source by the convertion of the electrical signal from the comparator into mechanical signal.

The film-blackening-area-measuring-equipment that includes all the variations of the embodiments as described above can also be used for other types of equipments, not to mention as an equipment of the chemical replenishing device for film processors. This invention is also applicable as an independent measuring instrument of film blackening area amount only.

Being such equipment as described in detail, the film-blackening-area-measuring-equipment according to the present invention ensures accurate and good measurement at all times even if the film detecting mechanism composed of a projecting and receiving units is deformed by external factors such as heat or when such troubles as wetting or contamination of the light conductors are resulted. Moreover, the signal processing circuit is adjusted accurately to a favourable condition before a film is inserted into the detecting mechanism, and film-blackening-area-measurement can be started under a stable condition at all times. Moreover, the present invention can be realized by quite a simple mechanism economically and with an exceedingly high durability. When applied as an equipment of the chemical replenishing device for film processors, this invention increases the processing ability of film processors and the effect is significant.

What is claimed is:

1. An apparatus for measuring film blackening area, having a detecting mechanism so composed to project light onto a film and to receive the light passed through the film by a receiver element, an amplification mechanism to amplify the output from the said receiver element, and a subtraction mechanism to subtract the amplified output from a reference signal, the difference between the said amplified output and the reference signal being calculated as a blackening signal to measure the blackening area of the film, comprising an amplification factor variable mechanism which is composed as the said amplification mechanism, and a comparator for comparing the output of the said amplification factor variable mechanism with the said reference signal, the output signal from the said comparator being supplied into the said amplification factor variable mechanism, the amplification factor being controlled depending on the magnitude of the said input signal and being fixed by a film insertion signal from a film feed mechanism.

2. An apparatus for measuring film blackening area, having a detecting mechanism so composed to project light onto a film and to receive the light passed through the film by a receiver element, an amplification mechanism to amplify the output from the said receiver element, and a subtraction mechanism to subtract the amplified output from a reference signal, the difference between the said amplified output and the reference signal being calculated as a blackening signal to measure the blackening area of the film, comprising a comparator for comparing the output of the said amplification mechanism with the said reference signal, and a light source control mechanism for controlling the intensity of the said light source by the output of the said comparator, the intensity of the said light source being kept at the controlled value by the film insertion signal from a film feed mechanism.

* * * * *